United States Patent [19]
Byers et al.

[11] Patent Number: 4,749,818
[45] Date of Patent: Jun. 7, 1988

[54] SYNTHESIS OF CIS-9-TRICOSENE

[75] Inventors: Jim D. Byers, Bartlesville; Charles A. Drake, Nowata, both of Okla.

[73] Assignee: Phillips Petroleum Company, Bartlesville, Okla.

[21] Appl. No.: 103,764

[22] Filed: Sep. 30, 1987

[51] Int. Cl.$^4$ ................................................ C07C 1/00
[52] U.S. Cl. .................................... 585/324; 585/328; 585/641
[58] Field of Search ........................ 585/324, 328, 641

[56] References Cited

U.S. PATENT DOCUMENTS

| | | | |
|---|---|---|---|
| 3,798,273 | 3/1974 | Cargill | 260/593 |
| 3,939,616 | 1/1976 | Meresz et al. | 424/84 |
| 3,948,803 | 4/1976 | Carney | 252/429 R |
| 4,006,065 | 2/1977 | Meresz et al. | 204/59 R |
| 4,016,220 | 4/1977 | Kupper et al. | 260/683 D |
| 4,018,884 | 4/1977 | Meresz et al. | 260/677 R |
| 4,234,752 | 11/1980 | Wu et al. | 585/640 |
| 4,609,498 | 9/1986 | Banasiak et al. | 260/410.9 R |

OTHER PUBLICATIONS

Journal of Organic Chemistry, vol. 37, p. 3971 (1972, Cargill et al.) Synthesis of the Housefly Sex Attractant.
Canadian Journal of Chemistry, vol. 52, pp. 1923–1924 (1974, Ho et al.) a Synthesis of Muscalure, the Housefly Sex Attractant.
J.C.S. Chem. Comm., pp. 735–736 (1973, Gribble et al.), One Step Synthesis of the Housefly Sex Attractant.
Tetrahedron vol. 33, pp. 1845, 1881–1883 (1977) Tetrahedron Report No. 34.
Bulletin of the Chemical Society of Japan, vol. 50, p. 2792 (1977, Abe et al.) a Synthesis of Muscalure.
The Total Synthesis of Natural Products, vol. 4, edited by John ApSimon (1981) pp. 20–23.

*Primary Examiner*—Curtis R. Davis
*Attorney, Agent, or Firm*—Williams, Phillips and Umphlett

[57] ABSTRACT

A process for the preparation of cis-9-tricosene is disclosed. Cis-1,9-octadecadiene, which may be obtained by the dehydration of oleyl alcohol, is metallated with an organomagnesium halide, producing cis-9-octadecenylmagnesium halide, which in turn is alkylated with n-pentyl halide to form the desired cis-9-tricosene.

11 Claims, No Drawings

SYNTHESIS OF CIS-9-TRICOSENE

BACKGROUND OF THE INVENTION

This invention relates to the preparation of cis-9-tricosene.

Cis-9-tricosene is a known sex pheromone for the common housefly (*Musca domestica* L.). It can be found in the cuticle and feces of the female housefly and it attracts the male fly, thus facilitating sexual reproduction.

Sex pheromones have been employed in a variety of ways for control of insect populations. For example, traps baited with appropriate pheromone compounds or mixtures can be employed to monitor for the presence of particular insects in a field. In this way, most efficient use of pesticides or other conventional means of insect control can be applied.

Traps as just described can also be used on a larger scale such that all insect pests in a given area may be lured to a trap. This technique is most effective where low-level insect populations exist. Such a trap fulfills the dual functions of monitoring for the presence of insect infestation and removing essentially all insects from the infested area, so long as the treatment program commences when insect populations are low.

The most promising means of controlling insect populations with pheromones is by permeating the atmosphere with the particular pheromone compound or mixture to which the offending insect responds. With sufficiently high levels of pheromone in the air, the searching insect becomes confused in its search for a mating partner. Since the insect cannot distinguish the artificially released pheromone from that released by a potential sex partner, propagation is greatly reduced as the likelihood of a successful encounter with a mating partner is greatly reduced.

In order to make this compound widely avilable for use in insect control, economic large scale synthetic conversion processes must be developed. While synthetic routes for the preparations of cis-9-tricosene have been disclosed in the prior art, the known routes suffer from the disadvantages of requiring multiple reaction steps with consequent low overall product yield, consumption of large quantities of reagents which do not contribute to the final product structure, use of expensive or specialized catalysts, and the like.

OBJECT OF THE INVENTION

It is thus an object of this invention to provide an efficient and economic process for the synthesis of cis-9-tricosene.

This and other objects will become apparent from further study of the disclosure and claims herein provided.

STATEMENT OF THE INVENTION

In accordance with the present invention, a process for the preparation of cis-9-tricosene is provided comprising:

(a) metallating cis-1,9-octadecadiene with an organomagnesium halide metallating agent in the presence of a metallating catalyst under metallating conditions suitable to produce cis-9-octadecenylmagnesium halide, (b) thereafter alkylating the product from step (a) with an n-pentyl halide in the presence of an alkylation catalyst under alkylation conditions suitable to produce cis-9-tricosene.

The metallation of cis-1,9-octadecadiene can be carried out in a variety of ways. Thus any suitable ratio of cis-1,9-octadecadiene/organomagnesium halide metallating agent can be employed in the presence of a wide variety of metallation catalysts. For the most efficient utilization of the cis-1,9-octadecadiene, a molar ratio of the cis-1,9-octadecadiene/organomagnesium halide metallating agent of about 1:1 is preferred, although good conversions are obtained with cis-1,9-octadecadiene/organomagnesium halide metallating agent ratios ranging from about 10:1 to about 1:10.

A wide variety of metallation catalysts are capable of promoting the metallation of cis-1,9-octadecadiene with the metallating agent. Our invention is not limited to the use of a specific catalyst in step (a), but any metallation catalyst that will promote the metallation of cis-1,9-octadecadiene with the organomagnesium halide metallating agent can be used. Metallation with organomagnesium halides is generally carried out in the presence of at least one transition metal that serves as the metallation catalyst. Suitable transition metals include nickel, titanium, vanadium and zirconium compounds. Examples of suitable metallation catalysts include, but are not limited to: titanocene dichloride, titanium tetrachloride, and tricyclopentadiene titanium chloride. The preferred metallation catalyst is titanocene dichloride. The metallating catalyst can be employed in any suitable amount that will serve to promote the metallation of cis-1,9-octadecadiene with the organomagnesium halide metallating agent. Generally the ratio of the moles of the metallating catalyst to moles of cis-1,9-octadecadiene is in the range of about 1:1–500 and preferably about 1:10–100.

The cis-1,9-octadecadiene can be obtained from any known source. Although pure cis-1,9-octadecadiene is desirable, it is generally obtained as a mixture with trans-1,9-octadecadiene. The cis/trans ratio of the 1,9-octadecadiene in step (a) will substantially influence the cis/trans ratio of the 9-tricosene product in step (b). Generally, the 9-tricosene cis/trans ratio of the final product is substantially equal to the 1,9-octadecadiene cis/trans ratio in step (a). Trans-9-tricosene is not known to have any biological activity as a sex pheromone, and is even known to act as a diluent when mixed with cis-9-tricosene. The higher the cis/trans ratio of the 9-tricosene, the higher the bilological activity. Generally in order to have any useful biological activity, a 9-tricosene cis/trans ratio of at least 3/7 is required.

The cis-1,9-octadecadiene can also be derived from oleyl alcohol which is a substance that is found in fish oils. Oleyl alcohol can also be derived from beef tallow, olive oil, and other natural resources, such as animal and vegetable fats and oils. Preferably the cis-1,9-octadecadiene is obtained by dehydration of oleyl alcohol in the manner taught in U.S. Pat. No. 4,234,752 issued Nov. 18, 1980 to Wu and Marwil (assigned to Phillips Petroleum Company) which broadly discloses the dehydration of alcohols to form olefins, the disclosure of which is herein incorporated by reference. Starting with a typical oleyl alcohol, having a cis/trans ratio of about 4/1, this Wu and Marwil method will yield 1,9-octadecadiene with a cis/trans ratio of about 4/1, yielding in step (b), a 9-tricosene with a cis/trans ratio of about 4/1.

Generally any organomagnesium halide metallating agent capable of selective reaction with the terminal double bond of the cis-1,9-octadecadiene can be used as a metallating agent. The organomagnesium halide metallating agent is of the formula RMgX wherein R is a $C_2$ to $C_{10}$ hydrocarbyl radical having at least one $\beta$ hydrogen, and X is Br, Cl or I. Exemplary compounds which satisfy the above formula include, but are not limited to, various Gringnard reagents, such as, for example, ethylmagnesium bromide, isopropylmagnesium bromide, n-butylmagnesium bromide and the like. The preferred organomagnesium halide metallating agent is n-butylmagnesium bromide.

The suitable operating temperature for metalling cis-1,9-octadecadiene with the organomagnesium halide metallating agent is in the range of about 20° to about 100° C. Preferably, the temperature is in the range of about 25° to about 35° C. In the metallation of cis-1,9-octadecadiene with the organomagnesium halide metallating agent, pressure is not important, but will generally be in the range of about 0 psig to about 2,000 psig. Preferably, the pressure is in the range of about 0 psig to about 25 psig. The reaction time for metallating cis-1,9-octadecadiene with the organomagnesium halide metallating agent will depend upon the desired degree of conversion, the reaction temperature and the catalyst utilized, but will generally be in the range from about 0.1 minute to about 24 hours. Preferably the reaction time will be in the range of about 5 minutes to about 120 minutes.

The metallation of cis-1,9-octadecadiene with the organomagnesium halide metallating agent can take place in a wide variety of solvents. Generally any solvent in which the reactants are soluble, will be a suitable solvent. Preferably, diethyl ether, tetrahydrofuran or dibutyl ether are used as solvents.

Once the metallation of the cis-1,9-octadecadiene is complete, the resulting cis-9-octadecenylmagnesium halide is ready for aklylation reaction with n-pentyl halide as detailed more fully below.

The alkylation of the cis-9-octadecenylmagnesium halide from step (a), with n-pentyl halide to form cis-9-tricosene, can be carried out in a variety of ways. Thus, any suitable ratio of the moles of n-pentyl halide to the original moles of cis-1,9-octadecadiene in step (a) can be employed in the presence of a wide variety of catalysts. For the most efficient utilization of the reactants, a molar ratio of the n-pentyl halide to the original moles of cis-1,9-octadecadiene in step (a) of about 1:1 is preferred, although good conversions are obtained with n-pentyl halide to cis-1,9-octadecadiene ratios ranging from about 10:1 to about 1:10. The n-pentyl halide used in step (b) is selected from the group consisting of n-pentyl chloride, n-pentyl bromide, and n-pentyl iodide. The preferred n-pentyl halide is n-pentyl bromide.

A wide variety of alkylation catalysts are capable of promoting the alkylation of cis-9-octadecenylmagnesium halide plus n-pentyl halide to produce cis-9-tricosene. Our invention is not limited to the use of a specific alkylation catalyst for this alkylation step but any alkylation catalyst that will promote the alkylation of cis-9-octadecenylmagnesium halide with n-pentyl halide can be used. Suitable alkylation catalysts include, but are not limited to: copper (I) iodide, copper (I) bromide, copper (I) chloride, and dilithium copper (I) tetrachloride. Preferably copper (I) bromide is used as the alkylation catalyst.

The alkylation catalyst can be employed in any suitable amount that will facilitate the alkylation of cis-9-octadecenylmagnesium halide with n-pentyl halide. Generally an amount of catalyst is added based on the original moles of cis-1,9-octadecadiene in step (a). Generally the molar ratio of the alkylation catalyst to the original number of moles of cis-1,9-octadecadiene in step (a) is in the range of about 1:1-500, and preferably in the range of about 1:10-100.

The operating temperature for alkalating cis-9-octadecenylmagnesium halide with n-pentyl halide so as to produce cis-9-tricosene is in the range of about $-60°$ to about 30° C. Preferably, the temperature is in the range of about $-10°$ C. to about 5° C. In this alkylation step, pressure is not important, but will generally be in the range of about 0 psig to about 2,000 psig. Preferably the pressure is in the range of about 0 psig to about 25 psig.

The time of the alkylation of cis-9-octadecenylmagnesium halide with the n-pentyl halide will depend upon the desired degree of conversion, the reaction temperature and the catalyst utilized, but will generally be in the range from about 0.1 minute to about 24 hours. Preferably the time of alkylation is in the range of about 5 minutes to about 120 minutes.

The alkylation of cis-9-octadecenylmagnesium halide with n-pentyl halide can take place in a wide variety of solvents. Generally any solvent in which the reactants are soluble will be suitable. Preferably, diethyl ether, tetrahydrofuran or dibutyl ether are used as solvents.

Any suitable method for product isolation can be employed. A typical reaction work-up involves several steps. First dilute acid equal in volute to the reaction mixture is added to the reaction mixture, causing a phase separation. Dilute aqueous HCL would be such an acid that could be used. Next, hexane, equal in volumetric amount to the organic layer, is added. The organic layer containing the cis-9-tricosene and hexane would then be separated. After a wash with an amount of a mild base equal in volumetric amount to the separated organic layer, the organic layer is again separated. Finally, the organic layer is ready for solvent removal by, for example distillation. The clean product is then recovered, typically by distillation at reduced pressure.

The following examples are provided in an effort to assist one skilled in the art to a further understanding of the invention, and yet not be unduly limitative of the resonable scope of the invention. The particular reactants, conditions, ratios and the like, are all intended to be illustrative of our invention, and not limitative of the reasonable and suitable scope thereof.

EXAMPLE I

Preparation of 1,9-Octadecadiene

Oleyl alcohol, having about a 4/1 cis/trans ratio, is dehydrated over gamma-alumina in the presence of nitrogen to produce 1,9-octadecadiene.

A trickle bed tubular reactor of 46 cm length and 1 cm I.D. was packed with gamma alumina (40 mesh, 24.8 gram). The reactor was heated to 340° C., and maintained at 30 psig during the run. The feed, containing 250 grams oleyl alcohol, and 2500 grams of hexane, was introduced into the top of the reactor at 2 mL/min. Nitrogen was introduced with the feed at 2 mL/min. The effluent from the reactor was then fed to a distillation column, to strip off the hexane. The final product was approximately 160 grams of cis-1,9-octadecadiene, and 40 grams of trans-1,9-octadecadiene.

EXAMPLE II

Preparation of Cis-9-Tricosene 5 grams of 1,9-octadecadiene, (produced in Example I) 7.5 mL n-butyl magnesium chloride (2.5 M in diethyl ether), 0.175 grams titanocene dichloride and 25 mL diethyl ether were place in a dry 1 liter round bottom flask equipped with a megnetic stirrer. The mixture was stirred for 3 hours at 25° C.

The reaction mixture was then cooled to −25° C. Next 25 mL tetrahydrofuran, 2.8 mL 1-bromopentane, and 1.14 grams cuprous bromide were added. The reaction mixture was held at −25° C. for 2 hours. Cooling coils were removed, and the reaction mixture allowed to slowly warm to 25° C. over the next 18 hours. Dilute HCl equal in volumetric amount to the reaction mixture was added, causing a phase separation. Hexane, equal in volumetric amount to the organic layer, was added. The organic layer was then separated. Next an aqueous sodium bicarbonate, equal in volumetric amount to the separated organic layer, was added to the separated organic layer. Once again the organic layer was separated and then fed to a distillation column. 2.6 grams of cis-9-tricosene were recovered.

The examples have been provided merely to illustrate the practice of our invention and should not be read so as to limit the scope of our invention or the appended claims in any way. Reasonable variation and modification, not departing from the essence and spirit of our invention, are contemplated to be within the scope of patent protection desired and sought.

That which is claimed is:

1. A process for the synthesis of cis-9-tricosene which comprises:
    (a) metallating cis-1,9-octadecadiene with an organo magnesium halide metallating agent of the formula RMgX in the presence of a metallating catalyst under metallating conditions suitable to produce cis-9-octadecenylmagnesium halide; wherein R is a $C_2$ to $C_{10}$ hydrocarbyl radical having at least one $\beta$ hydrogen, and X is Br, Cl or I,
    (b) thereafter alkylating the cis-9-octadecenylmagnesium halide from step (a) with an n-pentyl halide selected from the group consisting of n-pentyl bromide, n-pentyl chloride and n-pentyl iodide, in the presence of an alkylation catalyst under alkylation conditions suitable to produce cis-9-tricosene.

2. A process in accordance with claim 1 wherein step (a) is carried out at a temperature in the range of about 20° to about 100° C. and step (b) is carried out at a temperature in the range of about −60° to about 30° C.

3. A process in accordance with claim 1 wherein the metallation catalyst in step (a) is selected from the group consisting of titanocene dichloride, titanium tetrachloride and tricyclopentadiene titanium chloride.

4. A process in accordance with claim 1 wherein the alkylation catalyst is selected from the group consisting of copper (I), iodide, copper (I) bromide, copper (I) chloride and dilithium copper (I) tetrachloride.

5. A process in accordance with claim 1 wherein the cis-1,9-octadecadiene is obtained from the dehydration of oleyl alcohol.

6. A process in accordance with claim 1 wherein said cis-9-tricosene is recovered as a product of the reaction mixture.

7. A process in accordance with claim 1 wherein step (a) is carried out at a pressure in the range of about 0 to about 2,000 psig, and step (b) is carried out at a pressure in the range of about 0 to 2,000 psig.

8. A process in accordance with claim 1 wherein step (a) is carried out at a temperature in the range of about 25° to 35° C., and step (b) is carried out at a temperature in the range of about −10° to 5° C.

9. A process in accordance with claim 1 wherein the metallation catalyst is titanocene dichloride.

10. A process in accordance with claim 1 wherein the alkylation catalyst is copper (I) bromide.

11. A process in accordance with claim 1 wherein the organomagnesium halide is n-butylmagnesium bromide.

* * * * *